(12) United States Patent
Harper

(10) Patent No.: US 7,285,114 B2
(45) Date of Patent: Oct. 23, 2007

(54) HAND STERILIZING APPARATUS AND METHOD

(76) Inventor: William Anthony Harper, 16541 Redmond Way, Pmb 140, Redmond, WA (US) 98052

( * ) Notice: Subject to any disclaimer, the term of this patent is extended or adjusted under 35 U.S.C. 154(b) by 68 days.

(21) Appl. No.: 10/340,478

(22) Filed: Jan. 10, 2003

(65) Prior Publication Data

US 2004/0138631 A1 Jul. 15, 2004

(51) Int. Cl.
*A61M 35/00* (2006.01)
*B65D 83/04* (2006.01)
*B65D 85/42* (2006.01)

(52) U.S. Cl. ................ 604/289; 206/531; 206/532; 206/534; 206/538

(58) Field of Classification Search .......... 604/289–90; 401/132
See application file for complete search history.

(56) References Cited

U.S. PATENT DOCUMENTS

| | | | |
|---|---|---|---|
| 2,235,350 A | | 3/1941 | Anderson |
| 4,078,660 A | | 3/1978 | Lerro |
| 4,503,871 A | * | 3/1985 | Mendenhall ............... 132/311 |
| 4,526,474 A | * | 7/1985 | Simon ........................ 368/10 |
| 4,736,876 A | | 4/1988 | Kriss |
| 4,768,688 A | | 9/1988 | Harrigan |
| 5,261,570 A | | 11/1993 | Hippely |
| 5,429,301 A | * | 7/1995 | Franks ......................... 239/1 |
| 5,622,293 A | | 4/1997 | LeFevre |
| 5,927,548 A | * | 7/1999 | Villaveces .................. 222/82 |
| 5,938,363 A | | 8/1999 | Timms |
| 6,029,808 A | * | 2/2000 | Peck et al. ................. 206/210 |
| 6,173,866 B1 | | 1/2001 | Taylor |
| 6,228,375 B1 | | 5/2001 | Korcher |
| 6,234,357 B1 | | 5/2001 | Lewis |
| 6,273,260 B1 | * | 8/2001 | ColDepietro et al. ....... 206/532 |

(Continued)

FOREIGN PATENT DOCUMENTS

| | | | |
|---|---|---|---|
| GB | 1240515 | * | 7/1971 |
| ZA | 9504596 A | * | 8/1996 |

OTHER PUBLICATIONS

Earl, M. L.; Jackson, M. M. and Richman, L. S. (2001), Improved Rates of Compliance with Hand Antisepsis . . . Guidelines; *American Journal of Nursing*; Mar. 2001; 101 (3): 26-33.

(Continued)

*Primary Examiner*—Tatyana Zalukaeva
*Assistant Examiner*—Melanie J Hand

(57) ABSTRACT

This invention relates to devices and a method promoting the convenient use of hand sterilizing fluids and gels applied to reduce the hand-borne transmission of pathogens. While clean, disinfected hands are widely recognized as a principle means for controlling the spread of infections, disease, and similar health problems to both self and others, the prompt and repeated application of such materials as soap and water or waterless alcohol gels is necessary for maintaining a sanitary hand condition. This is particularly true for nurses, health care providers, veterinarians, elementary teachers, food handlers and others where rapid and continuous movement between patients, clients and tasks provides optimum conditions for cross-contamination. This invention of a convenient, wrist-mounted dispenser of hand sterilizing fluids in a blister package format advances the use of such materials to effectively control the spread of hand-borne pathogens.

26 Claims, 2 Drawing Sheets

U.S. PATENT DOCUMENTS

| | | |
|---|---|---|
| 6,283,334 B1 | 9/2001 | Mahaffey et al. |
| 6,540,109 B1* | 4/2003 | Klima et al. ............... 222/83.5 |
| 2001/0030140 A1* | 10/2001 | Mundt ........................ 206/534 |
| 2002/0112449 A1* | 8/2002 | Heath et al. ................... 53/440 |
| 2002/0171238 A1* | 11/2002 | Kozlowski et al. ........... 283/81 |
| 2004/0069673 A1* | 4/2004 | Dinges ........................ 206/484 |

OTHER PUBLICATIONS

Pittet, D. (2002), Promotion of Hand Hygiene: Magic, Hype, or Scientific Challenge?; *Infection Control and Hospital Epidemiology*; Mar. 2002; 23(3).

Boyce, J. M. (2000), Using Alcohol for Hand Antisepsis—Dispelling Old Myths; *Infection Control and Hospital Epidemiology*; Jul. 2000; 21(7).

Boyce, J. M. (2001) Antiseptic Technology: Access, Affordability, and Acceptance; Emerging Infectious Diseases; Mar.-Apr. 2001; 7(2): 231-233.

Dyer, D. L.; Shinder, A.; Shinder, F. (2000), Alcohol-free Instant Hand Sanitizer Reduces Elementary School Illness Absenteeism; Family Medicine; Oct. 2000; 32(9): 633-8.

\* cited by examiner

HAND STERILIZING APPARATUS AND METHOD

BACKGROUND OF THE INVENTION

The present invention relates generally to hand sanitizing fluid dispensers and, more particularly, to blister packaging which may be worn on the wrist or mounted elsewhere so as to promote timely and convenient use. The method describing the use of the wrist mounted dispenser identifies techniques that overcomes recognized and longstanding problems that contribute to inadequate hand sanitation which is the single most important factor in causing nosocomial infections.

Each year more than 2 million hospital acquired infections occur in the United States, costing some $4.5 billion in additional charges. The Center for Disease Control estimates more than one-third of healthcare associated infections can be prevented through better infection control programs of which hand cleaning is the centerpiece for reducing the spread of infection. Hospitals are only one of many organizations burdened with hand-borne disease costs. A recent school study found that classrooms that made hand sanitizing fluid dispensers simply available for use showed a 20% reduction in student absenteeism due to illness as well as a 10% decrease in teacher absenteeism. And these are but two groups that lend themselves to study. Much large population segments like commuters, food handlers, eaters, clerks, caregivers, and others share the same risks and could reasonable expect significant personal benefits from improved hand hygiene. The overall societal, economic and health impacts of hand-borne pathogens is enormous; it is the intent of the present invention to substantially reduce this debilitating situation.

Several recent articles provide an understanding of the current level of technology available and further describe the significant limiting problems the present art faces.

In March 2001 an American Journal of Nursing article ("impact Rate of Compliance with Hand Antisepsis . . . ") stated that 80,000 hospital deaths occur each year as a result of nosocomial infections contracted during hospital stays. Further, that "it's common knowledge that the hands of heath care workers can carry disease-causing organisms from one patient to another and that hand antisepsis before and after each patent contact is crucial to the prevention and control of nosocomial infection."The reasons most often cited by hospital staff for failing to clean their hands adequately are inconvenience and no time. Given the hectic and demanding nature of their workload these are not excuses but simply statements of reality. That convenience and time are critical factors in maintaining hand sanitation is underscored by the finding in this study that placing hand sanitizing fluid dispensers "in the hallways outside patient rooms were nearly 30 times more likely to be used than dispensers mounted anywhere inside the rooms." Yet the most disturbing finding of this study was that full compliance with hand antisepsis guidelines was an unrealistic goal. That while hand sanitizing fluids took less time than washing and the placement of numerous dispenser bottles made matters somewhat more convenient, even with the heightened attention impact of the study itself (the Hawthorne effect), compliance did not achieve more than 60% at any time during the study. And it is well understood that over time, after the study is done and gone, a drift back to much lower compliance rates is inevitable; the dispenser bottle becomes just one more thing in the room, like soap at the sink, to be used when time and convenience allows.

In March 2002 an article in Infection Control and Hospital Epidemiology ("Promotion of Hand Hygiene: Magic, Hype or Scientific Challenge?") restates the conditions for promoting adequate hand hygiene. "Among enabling factors, engineering control must be considered for the successful promotion of hand hygiene. In particular, it involves making hand hygiene easy, convenient, and possible in a timely fashion." Another observation made is that the higher rates of compliance seen in studies can only be sustained when some form of cost-effective, non-intrusive monitoring is invented. "My personal opinion is that obtaining a sustained and never-ending Hawthorne effect associated with improved compliance with hand hygiene and decreased infection and cross-transmission rates should be the dream of every hospital epidemiologist. Let's find a cost-effective way to induce it." This need has remained unfilled until now.

In July 2000 another article in Infection Control and Hospital Epidemiology ("Using Alcohol for Hand Antisepsis—Dispelling Old Myths") the qualities and values of alcohol-based hand antiseptics are described. The author points out the cost benefits of hand sanitizing fluids in hospitals. " . . . administrators should consider that modest increase in acquisition costs for alcohol-based hand hygiene products are tiny in comparison to excess hospital costs associated with nosocomial infections. If increased use of an alcohol gel or rinse reduces the number of serious nosocomial infections by a few a year, the cost savings from prevented infections should more than offset incremental costs of using alcohol-based preparations." These offset costs are those the hospital would charge as operational costs. Not considered are the much more substantial costs of the damage awards issuing from pain and suffering lawsuits won by patient and their attorneys for the hospital's failure to follow best practice protocols.

In March 2001 an article in Emerging Infectious Diseases ("Antiseptic Technology: Access, Affordability, and Acceptance") further reinforces the findings that time and convenience are critical compliance factors. Detailed costs of implementing a hand hygiene program are also provided.

A final article in the October 2000 issue of Family Medicine ("Alcohol-free Instant Hand Sanitizer Reduces Elementary School Illness Absenteeism") reports a remarkable reduction in absenteeism when hand sanitizers were introduced in public school classrooms. Results showed students using hand sanitizing fluids "were found to have 41.9% fewer illness-related absence days, representing a 28.9% and a 49.7% drop in gastrointestinal- and respiratory-related illness, respectively. Conclusion: Daily use of the instant hand sanitizer was associated with significantly lower rates of illness-related absenteeism." In this study the close monitoring and continual instruction of the test group by teachers largely abrogated the issues of time and convenience. Nevertheless, it clearly indicates the significant impact consistent and rigorous hand sanitation can have in schools and the implications for parallel benefits at all levels of society are obvious. As the reports point out in describing the interlinking cost of disease "Even if one doesn't have school-age children, it is necessary to understand the importance and benefits of good hand hygiene, not only in clinical practice but also in the greater community. Vital tax dollars will be saved on expenses for remedial student services and employee work time by this simple and effective way to decrease illness-related absenteeism."

That improved hand hygiene can be achieved by using various hand sanitizing fluids is beyond question, the problems preventing this known technique for achieving a high degree of use (compliance) are equally understood as being time and convenience. A compact wrist mounted at hand package dispensing unitized hand sanitizing fluids can largely overcome these twin factors. No such product is in the marketplace today and a review of commercial literature found no such product description or even the suggestion of such a solution. Prior art as described in the patent literature offered few relevant discoveries and these will be discussed as follows. The patent art can best be divided into three subject areas: Wearable Liquid Dispensers; Carried Hand Sanitizing Fluid Dispensers; and Blister Packaging.

There have been numerous prior art devices for dispensing liquids, eight that are wearable and relevant in some fashion are as follows:

Anderson U.S. Pat. No. 2,235,350 disclosed in 1941 a wrist bracelet with a hollow chamber for holding a liquid, dischargeable out an opening controlled by a needle valve. The lotion is dispensed by a gravity flow from the bracelet.

Lerro U.S. Pat. No. 4,078,660 disclosed a blister style package attached as a bracelet to a wrist. The cavity formed by the blister contained instructions and medicine for use in an emergency. The purpose of the alert bracelet with a hermetically sealed pill was to assure that emergency medication would be available anywhere under any condition.

Kriss U.S. Pat. No. 4,736,876 disclosed a dispenser of body lotions worn on the wrist. It employed the use of flexible sidewalls whereby upon removal of the cap and squeezing some lotion would be discharged. The dispenser was designed for use in the shower whereby the user could select soap, shampoo, and conditioner from various packets on their wrist.

Harrigan U.S. Pat. No. 4,768,688 discloses a suntan lotion bracelet in the shape of a flexible tube body filled with lotion. Caps at each end, with joining male and female aspects, form a clasp by which the tube forms a bracelet.

Hippely U.S. Pat. No. 5,261,570 discloses a flexible liquid container for suntan lotion, perfume, or repellent to be hung around the neck or carried in a pocket. The advancement in the art was the inclusion of a flexible mirror mounted on the sidewall of the dispenser.

LeFevre U.S. Pat. No. 5,622,293 disclosed another flexible liquid tube container with novel barbed or barrel end caps that formed a clasp arrangement for encircling the wrist.

Timms U.S. Pat. No. 5,938,363 disclosed a lotion dispenser that incorporates various cavities that accept replaceable lotion filled cartridges. The dispenser could be carried in a pocket, notebook or purse.

Taylor U.S. Pat. No. 6,173,866 disclosed a wearable container of potable liquid attached to the wrist by Velcro fasteners.

None of the eight wearable liquid dispensers disclosed or suggested a wrist mounted or blister packaged device associated with dispensing hand sanitizing fluids. Three patents in the Carried Hand Sanitizing Fluid Dispensers group are as follow:

Kocher U.S. Pat. No. 6,228,375 discloses a small single-use disposable container of hand sanitizing fluids, similar to the catsup packet at a fast food restaurant. It is to be carried in the pocket and used discreetly for dispensing an application as needed.

Lewis U.S. Pat. No. 6,234,357 discloses a two-part dispenser arrangement consisting of a holster and a removable flexible wall container for ready deployment. A key advancement to the art disclosed is that the holster's mounting swivels and thus keeps the product container inverted to assure the gel is ready at the cap for immediate discharge.

Mahaffey U.S. Pat. No. 6,283,334 disclosed the same dispenser of Lewis '357 with additional claims for wearability and multiple types of dispensers used with a common mounting element.

None of the three Carried Hand Sanitizing Fluid devices disclosed or suggested a wrist mounted or blister packaged device associated with dispensing hand sanitizing fluids. The prior art for blister packaging as a disposable dispensing apparatus has a long and extensive history. Bubble or blister packaging has been utilized for the simple holding of a pill to complex configurations adapted to contain a hydrophilic contact lens in a sterile aqueous solution. But nowhere was it found in the review that hand sanitizing fluids have been packaged for wrist attachment or mounted as described by the present invention.

The above discussed current practices and known forms of dispensers and packing, all were found deficient in several respects. Significantly, none of the above references taken in part or as a whole presents a convenient, timely, and effective way of facilitating the use of hand sanitizing fluids achievable by means of a wrist mounted dispenser. None overcome the recognized problems of time and convenience provided by the advancement of the art the present invention clearly achieves.

SUMMARY OF THE INVENTION

The present invention recognizes and addresses the foregoing disadvantages and shortcomings of the prior art. Accordingly it is a primary intent of the present invention to provide a distinctly novel product concept and equally important innovative method using that concept to overcome both problems of timely use and inconvenience which have previously curtailed the effective use of hand sanitizing fluids. Further, in one embodiment of the product, namely the plural blister packaging, there are inherent design features which foster ongoing compliance monitoring without intrusive overhead or additional expense.

At its elemental base the present invention can be simply described as use of an attachable, disposable blister well package of hand sanitizing fluid to disperse fluid for application to the hands. When the package is specifically attached to the wrist several benefits are immediately apparent: it is always at hand for instant use; it is close at hand to the point of application; its very presents on the wrist reminds the user to use the fluid; it takes no time to retrieve and return to pocket; and it requires no walking to and from a distant dispenser. These numerous at hand advantages have given the invention its name, the Athand™ system. From the simple concept of the wrist-mounted dispenser a number of expressions introduce a wide range of other advantages as will be discussed by way of the examples provided in the detailed descriptions of the preferred embodiments. Therefore:

It is an object of the present invention to mount a dispenser of hand sanitizing fluid on the wrist of the user.

It is an object of the present invention to mount a dispenser of hand sanitizing fluid on the body of the user.

It is an object of the present invention to provide a wearable product dispenser with an facile opening means.

It is an object of the present invention to provide a means and method to reduce the spread of hand-borne pathogens by reducing time and inconvenience of use.

It is an object of the present invention to provide unitized doses of hand sanitizing fluid in a blister packaging format to speed access and eliminate the immediate need for garbage disposal.

It is an object of the present invention to remind the wearer of the need for hand sanitation by providing continual visual and tactile cues created by the dispenser's ever-present proximity to the hands.

It is an object of the present invention to provide a form of inconspicuous packaging of hand sanitizing fluid dispensers.

It is an object of the present invention to provide an inexpensive disposable hand sanitizing fluid dispenser.

It is an object of the present invention to provide an adhesive backing for quick, easy, and inexpensive mounting on the body or elsewhere.

It is an object of the present invention to provide a means for commercial advertising and promotion incorporated with the hand sanitizing fluid dispenser.

It is an object of the present invention to reduce cross contamination through use of multi-user dispensers.

Other objects, features and aspects of the present invention are described in greater detail by the following exemplary embodiments. It is to be understood by one of ordinary skill in the art that these are exemplary embodiments only, and are not intended as limiting the broader aspect of the present invention, which broader aspects are embodied in the exemplary constructions.

BRIEF DESCRIPTION OF THE DRAWINGS

The invention will be better understood and objects other than those set forth above will become apparent when consideration is given to the following detailed description thereof. Such description makes reference to the annexed drawings wherein.

The same numbers reference the same elements in all the various figures.

DETAILED DESCRIPTION OF THE PREFERRED EMBODIMENTS

The present invention can best be understood by several examples that illustrate how a relatively flat blister package containing hand sanitizing fluids can be attached to a wrist and otherwise mounted to reduce the time and convenience problems known to curtail satisfactory compliance levels for hand sanitation.

EXAMPLE 1

Wrist Blister Dispenser

Figure 1:
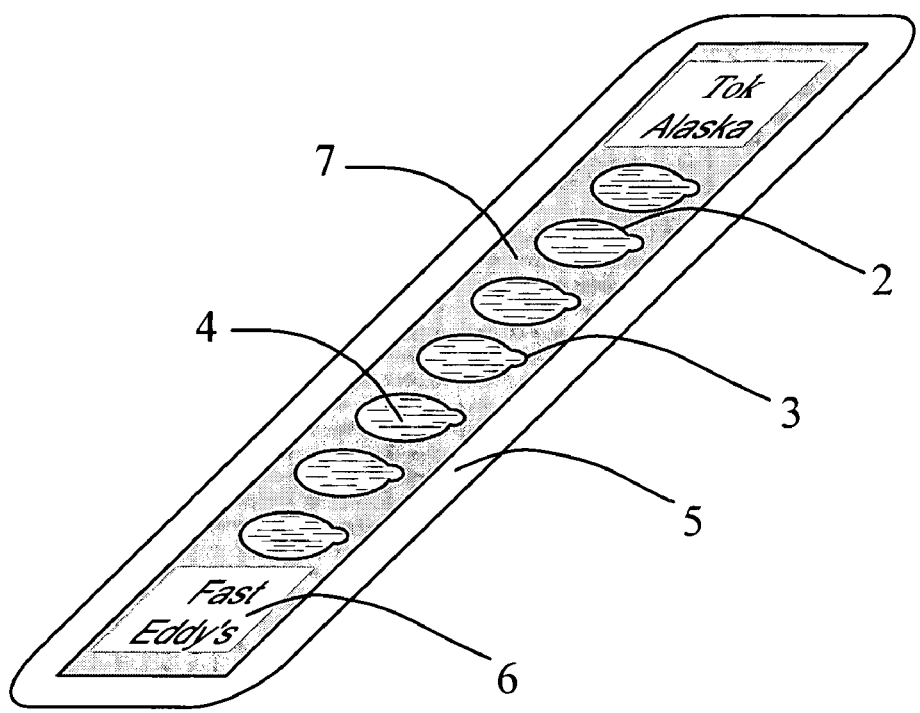
FIG. 1 is a frontal perspective view of a simple embodiment of a dispenser package with multiple blister wells 2 formed in a top film, each containing a single application of hand sanitizing fluid 4, sealed to a stiff backing 5 in accordance with the principle of the present invention.
Figure 2:
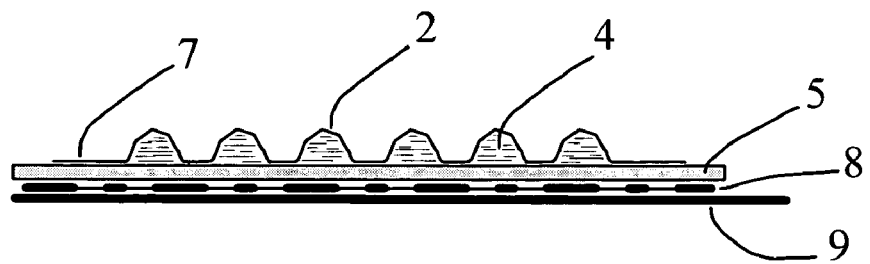
FIG. 2 is a cross-sectional side view showing the relationship of the plural wells 2, backing 5, sealing areas 7, affixing adhesive 8 and a removable cover 9 on the adhesive.

The dispenser is in the form of a common blister package card that contains a plurality of dosage wells containing hand sanitizing fluid. Each well is spaced at uniform distances from others and are typically 12 in number on the card's surface, although of course, various other alternative embodiments are easily imaginable and useful. Typically the number of wells might range between 2 and 30. Each of the wells has one basic requirement, the ability to hold and preserve the quality of the hand sanitizing fluid, typically a viscous liquid in the form of a gel such as found in several commercial offerings sold under the general designation of hand sanitizers and hand sterilizers. Each cell contains about 2 milliliters of hand sanitizing fluid, although the range of the dosage amount for an individual application can easily vary from about 0.5 ml to 5 ml depending on the product's formulation, sanitizing strength, and the coverage desired. The blister forming the well is flexible so that sufficient purposeful pressure on this flexible surface can release the hand sanitizing fluid within at a predetermined point such as rupturing at a specific point created in the design of the blister's surface. To permit adequate pressure buildup, a relatively stiff and impervious backing placed in a sealing arrangement with the blister cover is required. This backing was applied in the manufacturing process after the blister wells were formed in the cover and filled with hand sanitizing fluid, sealed to the cover by heat or some like means, and thus forming one side of the container (gel filled cavity). Graphic representation of an embodiment of the multi-well, single dose dispenser package is shown in FIGS. 1 and 2. Seven blister wells 2 formed of flexible polymeric film (2-mil clear, coextruded polypropylene/polyvinyldichloride/polypropylene) enclose and contain a hand sanitizing fluid 4 (62% ethanol). The film with its filled wells 2 has a peripheral seal 7 with a relatively stiff backing 5 that facilitate handling by hands of varying size and strength and effectively lids each of the wells 2. Creation of the seal can be achieved by a number of means well known in the art, herein the common technique involving heat and pressure is used to create the seal 7. Also illustrated is a release point 3 in the form of a weakened area of each well 2 wall created by design during the molding of the well 2 in the film to form a predetermined point for fluid 4 release. Further illustrated in FIG. 1 is a mark 6 functioning as a simple cuing means for the package. FIG. 2 shows all the elements of FIG. 1 laid out as a cross-section which further depicts a package attachment means herein shown as an adhesive 8 with a removable cover 9. The encapsulated hand sanitizing fluid is surrounded and sealed by impervious material that both retains and preserves the desirable properties of the fluid. The backing can do more than just form one side of a container; by extending its length beyond the blister cover wrapping straps are formed capable of encompassing a wrist. When the straps are further equipped with adhesives near the ends, the backing becomes a means for attaching the entire blister package to the wrist. Of course the adhesive forming a closure means could be any of other connecting types including buckles, buttons, clasps, fasteners, holes, loops, magnets, pins, rivets, twists, ties, or Velcro hooks and loops. By attaching the blister package to the wrist by means of the backing straps, the flexible blisters are exposed to access. With sufficient pressure applied to a given flexible blister by the wearer in the form of a finger or thumb of the opposite hand a predetermined amount of hand sanitizing fluid is released from the well to be conveyed by the finger or thumb to the hands for application. The shape and design of the blister can greatly facilitate this fluid release while also contributing to the overall ergonomic aspect of the dispenser package. Some geometric forms anticipated include a circular ring, cone, cube, cylinder, disc, ellipsoid, frustum, hemisphere, oval, paraboloid, prism, pyramid, rectangular prism, spheroid and whole or partial combinations thereof. These form elements can be used to design where the rupture release point is to be by focusing the pressure buildup to a specific designated point and soften the burst out flow. Alternatively, the blister surface can be simply weakened by thinning a designated area of the blister wall during formation of the well. Another form of release is a group of release points characterized by a self-closing slit or puncture opening. The overall aspect of the disposable dispenser package attached to the wrist is of a device low in profile, lightweight, easily attached, non-interfering, readily accessible, and always at hand.

EXAMPLE 2

Blister Card Multi-Dose Package

Figure 3:
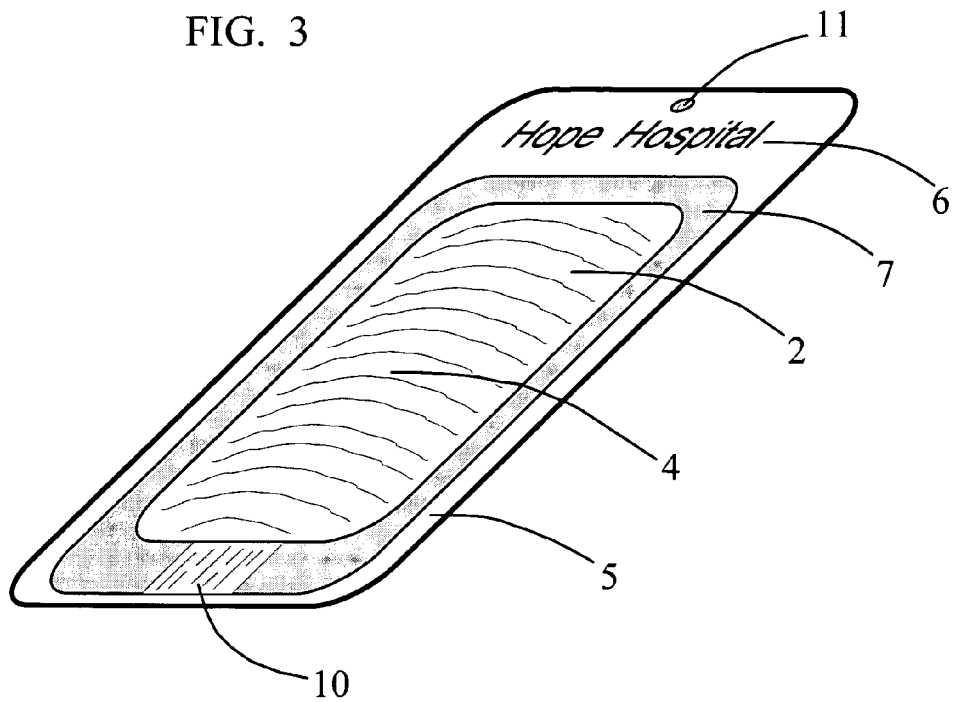
FIG. 3 is a frontal perspective view of a simple embodiment of a dispenser package with a single blister well 2 formed in a flexible top film containing a multiple application of hand sanitizing fluid 4, sealed to a stiff backing 5 in accordance with the principle of the present invention.
Figure 4:
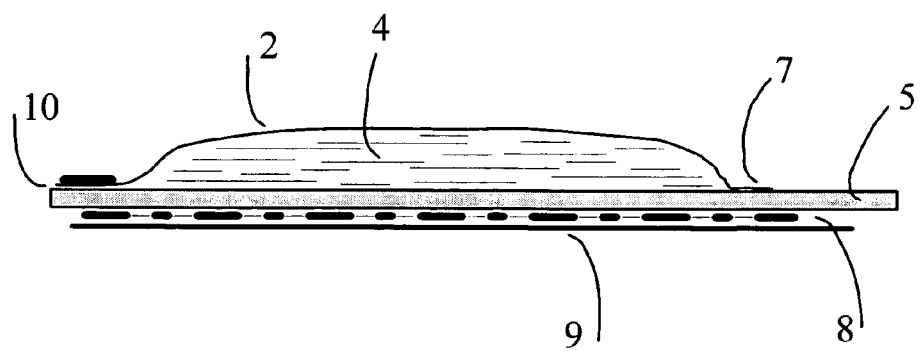
FIG. 4 is across-sectional side view showing the relationship of the single well 2, backing 5, sealing areas 7, affixing adhesive 8, and a removable cover 9 on the adhesive.

The dispenser is in the form of a common blister package card that contains only one well containing hand sanitizing fluid. Graphic representation of an embodiment of a single well, multiple dose dispenser package is shown in FIGS. 3 and 4. A single well 2 formed of flexible polymeric film (2-mil clear, coextruded polypropylene/polyvinyldichloride/polypropylene) enclose and contain multiple doses of hand sanitizing fluid 4 (62% ethanol). The film with its filled wells 2 has a peripheral seal 7 with a relatively stiff backing 5 that facilitate handling by hands of varying size and strength and effectively lids each of the wells 2. Creation of the seal can be achieved by a number of means well known in the art, herein the common technique involving heat and pressure is used to create the seal 7. Also illustrated is a release point 10 for the fluid 4 in the form of a self-closing tension valve which opens under pressure generated by finger pressure on the flexible film forming the well 2 surface. Further illustrated in FIG. 3 is a mark 6 functioning as a simple cuing means for the package. A hole 11 for a lanyard or clip fastener in the package provides an example of one of many possible attachment mechanisms. FIG. 4 shows the elements of FIG. 3 laid out as a cross-section which further depicts another example of a package attachment means herein shown as an adhesive 8 with a removable cover 9. The amount of fluid is typically 5 to 60 milliliters and permits several applications dosages to be released as contrasted with the single-use emptying of the blister dispenser/containers of Example 1. The strapping system, pressure manipulations, blister forms, closure means, and strap attachment descriptions of Example 1 are also incorporated in this example. However, in that the dispenser is to provide multiple dose applications the predetermined fluid release openings need to be closed following a discharge of fluid to preserve the remaining material. This valve requirement can be met by any of a vast number of types known to the art and all are envisioned under the general engineering subject of valves. Two in way of example and by their simplicity that could be of particular value on a disposable dispenser package are herein described. The first, is a simple one-way flap valve that, working in conjunction with the well-know clogging properties of viscous liquids and gels like the hand sanitizing fluids currently marketed, forms an adequate sealing means after each dosage release. The second is a simple self-closing slit or puncture opening that again partially relies on the clogging and evaporative properties of the hand sanitizing fluid to seal the opening.

EXAMPLE 3

Blister Card Package

The dispenser is in the form of a common blister package that contains the plurality of dosage wells described in the manner of Example 1. All other descriptions of Example 1 are herewith included in this example with the exception of the strapping portion for attachment to the wrist. In this example the exposed backing of the relatively flat card of the blister card dispenser package has an adhesive coating to act as an attachment means. By this adhesive means the card can be placed on the wrist directly without the need for a strapping means. Of course an appropriate adhesive should be used, a nonpermanent type would likely appeal to most wearers. The adhesive card as herein embodied could be applied to any part of the user's body including an ankle, forearm, hand, head, leg, neck, torso, wrist and combinations thereof as found appropriate. The adhesive card could also be applied to clothing or other items worn on the body like the ubiquitous identification passes hung from the neck. Additionally, the card could be applied to objects for convenient access like a bed, briefcase, cash register, crib, desk, incubator, lunch box, notebook, personal property items, purse, toolbox, vehicle, workstation and other like things. Also envisioned are attachment means other than adhesives which would include buckles, buttons, clasps, fasteners, holes, loops, magnets, pins, rivets, screws, twists, ties, Velcro and the like.

EXAMPLE 4

Use Stimulus Method

By way of the previous examples it has become obvious what physical forms the present invention can manifest. Equally important, however, is getting these physical expression used in a timely and convenient manner so the objective of the whole matter, sanitary hands not conveying pathogens in this instance, is actually accomplished. From the review of the literature it is clear the benefits of clean hands is recognized but time and convenience factors cut short every effort at compliance. What is needed is not only a diminishment of these twin factors to a level of inconsequence but further, to provide an ever-present stimulus to remind the subject of the need to sanitize their hands in a timely manner. The method of the present invention provides this technique. By attaching a package containing hand sanitizing fluid to the wrist the wearer is continually reminded of the need for hand sanitizing by the visual and tactile cues provided by the package's proximity to the hands. The ease of access, minimal time requirement, and general convenience of the proximate location coupled with prompted flashes of awareness provided by these cues means a hand sanitation action naturally follows when desirable. Perception of the package leading to the above chain of action can be heightened by the package's color, colors and markings. These markings can serve a number of other useful functions also; the marking may be made up of advertising messages, call numbers, codes, company names, decorative art, facility names, formulas, instructions, logos, notes, schedules, and similar meaningful images. Tactile perception can be heightened by various physical properties of the package including its weight, form, surface and fit. And the form of heightened perception need not be a passive property, but could also employ such techniques as the package reflecting light or even generating it. Vibration and sound are other forms of active engagement, and like the generated light could be scheduled, unscheduled, or on demand as appropriate. Any and all means, passive and active, subtle and overt, which the wrist or otherwise mounted dispenser package can employ to heighten perception leading to a timely act of hand sanitation are envisioned. An additional group of advantages presented by the above described method is that the package is a disposable personal item and thus minimizes contamination during and after use. Further, not being shared among many users the problem of cross contamination is eliminated. And being worn the actions necessitating a container's retrieval and return to a pocket are fully eliminated.

Throughout this application various publications are referenced. The disclosures of these publications in their entireties are hereby incorporated by reference into this application in order to more fully describe the state of the art to which the invention pertains.

While preferred embodiments of the invention have been discussed and described, modifications and variations may be made thereto by those of ordinary skill in the art without departing from the spirit and scope of the present invention, which is more particularly set forth in the appended claims. In addition, it should be understood that aspects of the various embodiments may be interchanged both in whole or in part. Further, those of ordinary skill in the art will appreciate that the foregoing description is by way of example only, and is not intended to be limitative of the invention so further described in such claims.

What is claimed is:

1. A hand sanitizing product, comprising: at least two flexible blister wells, each said blister well adapted to retain and preserve a single application amount of hand sanitizing fluid; a relatively stiff and impervious backing means placed in a common sealing arrangement with said blister wells; and said flexible blister wells release retained said hand sanitizing fluid by a release means located in the walls of said blister wells when sufficient purposeful pressure means is applied to the surface of a single said flexible blister well.

2. The product of claim 1 wherein there are a plurality of blisters.

3. The product of claim 2 wherein the number of blisters is typically between 2 and 30.

4. The product of claim 1 wherein the amount of said sanitizing fluid in each said blister is typically 0.5 to 5 milliliters.

5. The product of claim 1 further comprising the aspect of a relatively flat card.

6. The product of claim 1 further comprising the capacity of said backing to provide an attachment means suitable for affixing said product.

7. The product of claim 6 wherein said attachment means is selected from an affixing group consisting of adhesives, buckles, buttons, clasps, fasteners, holes, loops, magnets, pins, rivets, screws, twists, ties, Velcro and/or combinations thereof.

8. The product of claim 1 wherein said purposeful pressure means is applied by finger and/or thumb.

9. The product of claim 1 wherein said blister is shape in a geometric form selected from a group comprising a circular ring, cone, cube, cylinder, disc, ellipsoid, frustum, hemisphere, oval, paraboloid, prism, pyramid, rectangular prism, spheroid and/or partial combinations thereof.

10. The product of claim 1 wherein said release means of said sanitizing fluid is at a predetermined point in the wall of said blister wells.

11. The product of claim 10 wherein said predetermined point is formed by rupturing a weakened area in the wall of said blister wells created by design.

12. The product of claim 10 wherein said predetermined opening is a self-closing slit or puncture opening.

13. The product of claim 1 wherein said backing with said attachment means is affixed to an identification badge worn around the neck.

14. The product of claim 1 wherein said backing with said attachment means is affixed to worn clothing.

15. The product of claim 1 wherein said backing with said attachment means is adapted to be worn or attached to or affixed to a human body part by means of a strapping device, lanyard, or directly to the skin.

16. The product of claim 15 wherein said body part is selected from a group comprising an ankle, forearm, hand, head, leg, neck, torso, wrist and/or combinations thereof.

17. The product of claim 1 wherein said backing with said attachment means is affixed to an object.

18. The product of claim 17 wherein said object is selected from a group comprising a bed, briefcase, cash register, crib, desk, incubator, lunch box, notebook, personal property item, purse, toolbox, vehicle, workstation and/or combinations thereof.

19. The product of claim 1 wherein said product further incorporates visual and/or tactile cuing means that heightening perception of said product.

20. The product of claim 19 wherein said cuing means are selected from a group consisting of a color, colors, fit, form, markings, shape, structure, surface, texture, weight, and/or combinations thereof.

21. The product of claim 20 wherein said markings are selected from a group consisting of advertising messages, call numbers, codes, company names, decorative art, facility names, formulas, logos, meaningful images, notes, schedules, and/or combinations thereof.

22. The product of claim 19 wherein said cuing means employs reflected light.

23. The product of claim 19 wherein said cuing means emits a steady or pulsing generated light.

24. The product of claim 19 wherein said cuing means emits a vibration and/or sound.

25. The product of claim 23 or claim 24 wherein said cuing means emits a cue on a scheduled, unscheduled, and/or on-demand basis.

26. The product of claim 1 wherein said product is adapted to be worn or attached to an individual becomes a personal dispenser of hand sanitizing fluid and thereby reduces cross contamination thru usage by multiple users.

* * * * *